United States Patent [19]

Schillawski

[11] Patent Number: 4,513,152

[45] Date of Patent: Apr. 23, 1985

[54] CHLORAL PURIFICATION

[75] Inventor: Richard D. Schillawski, Boulder City, Nev.

[73] Assignee: Stauffer Chemical Company, Westport, Conn.

[21] Appl. No.: 538,698

[22] Filed: Oct. 3, 1983

[51] Int. Cl.³ .............................................. C07C 45/80
[52] U.S. Cl. .................................................. 568/492
[58] Field of Search ......................................... 568/492

[56] References Cited

U.S. PATENT DOCUMENTS

| | | | |
|---|---|---|---|
| 2,443,183 | 6/1948 | Cass | 568/492 |
| 2,478,152 | 8/1949 | Cass | 568/492 |
| 2,584,036 | 1/1952 | Mahoney et al. | 568/492 |
| 2,606,864 | 8/1952 | Cave et al. | 568/492 |
| 2,616,929 | 11/1952 | Rosin | 568/492 |
| 2,768,173 | 10/1956 | Wohlers et al. | 568/492 |

Primary Examiner—Werren B. Lone
Attorney, Agent, or Firm—Vivienne T. White

[57] ABSTRACT

The invention is a process for drying and purifying wet crude chloral which process comprises contacting the wet crude chloral with sulfuric acid solution in such manner that the solution in contact with the chloral has a concentration of about 50 percent or below, recovering the chloral, contacting the recovered chloral with concentrated sulfuric acid and utilizing the effluent acid recovered from the second contacting operation in first contacting of a subsequent process operation. Multistage, countercurrent flow arrangements are described. Hydrogen chloride and other acidic impurities are also substantially removed.

30 Claims, 2 Drawing Figures

CHLORAL PURIFICATION

FIELD OF THE INVENTION

The invention is directed to the purification of chloral derived from aqueous chlorination of acetaldehyde.

RELATED ART

Chloral historically has been produced by the chlorination of ethanol or acetaldehyde. The ethanol processes are exemplified by the following reaction sequence:

$$2\ CH_3CH_2OH + 4\ Cl_2 \longrightarrow \underset{\text{chloral alcoholate}}{CCl_3CH(OH)OCH_2CH_3} + 5\ HCl$$

$$CCl_3CH(OH)OCH_2CH_3 + H_2SO_4 \longrightarrow$$

$$\underset{\text{chloral}}{CCl_3CHO} + \underset{\substack{\text{ethyl acid}\\\text{sulfate}}}{CH_3CH_2SO_4H} + H_2O$$

A prominant side reaction of the above is:

$$CH_3CH_2OH + HCl \longrightarrow \underset{\substack{\text{ethyl}\\\text{chloride}}}{CH_3CH_2Cl} + H_2O$$

The ethanol processes, because of loss of ethanol through byproduct ethyl chloride generation and ethyl acid sulfate production, and environmental and waste disposal problems associated with production of these materials, have been largely replaced by acetaldehyde chlorination exemplified by the following:

$$CH_3CHO + 3Cl_2 \rightarrow CCl_3CHO + 3\ HCl$$

Chloral is an extremely reactive and unstable compound which will combine with many chemical substances, including itself, or decompose.

The usual commercial practice of manufacturing chloral from acetaldehyde involves adding water to the material undergoing chlorination to inhibit decomposition of dichloroacetaldehyde and chloral by their reactions with chlorine. Chloroform and carbon tetrachloride result from decomposition, probably through the reactions:

$$CHCl_2CHO + 2\ Cl_2 \rightarrow CHCl_3 + HCl + CCl_2O$$

$$CCl_3CHO + 2Cl_2 \rightarrow CCl_4 + HCl + CCl_2O$$

Presumably the decomposition reactions are inhibited by formation of the hydrates:

$$CHCl_2CHO + H_2O \rightarrow CHCl_2CH(OH)_2$$

$$CCl_3CHO + H_2O \rightarrow CCl_3CH(OH)_2$$

The hydrates are much more stable and therefore production of crude chloral containing only trace amounts of dichloroacetaldehyde, without significant chloroform and carbon tetrachloride co-production, can be accomplished. The chlorination reaction in addition generates significant amounts of byproduct hydrogen chloride gas (HCl)some of which tends to be absorbed by the wet crude chloral. To produce the purified chloral from the wet crude product, water and HCl must be removed.

U.S. Pat. No. 774,151 discloses distilling crude chloral alcoholate after it is contacted with sulfuric acid in a reservoir prior to further purification with chalk to neutralize acidity.

U.S. Pat. Nos. 2,443,183 and 2,478,152 disclose treatment of crude chloral alcoholate with an equal volume of concentrated sulfuric acid ($H_2SO_4$) and separation by distillation.

In U.S. Pat. No. 2,478,741 concentrated $H_2SO_4$ is utilized in a complicated combination with distillation to produce purified chloral.

U.S. Pat. No. 2,768,173 discloses purifying crude chloral in a two step process comprising using a $H_2SO_4$ wash with a minimum 60 percent concentration, preferably 70 to 85 percent, and a second wash with concentrated $H_2SO_4$. The sulfuric acid-chloral mixtures are separated by liquid-phase separations.

German Pat. No. 955,589 discloses reacting chloral alcoholate in vapor phase with sulfuric acid in a packed column to produce a dry chloral product.

British Pat. No. 661,092 discloses a process, Col. 3, lines 92-109, in which crude chloral is heated "with sufficient sulfuric acid to give about 60 parts of sulfuric acid per 40 parts of water and is then distilled without rectification . . . The distillate is treated with additional (fresh) sulfuric acid . . . After mixing, the sulfuric acid, containing practically all of the water, is . . . separate(d) . . . and stored for use in the first-stage . . . " of the purification process which uses countercurrent flows of the chloral and sulfuric acid solutions.

A variety of solvent extraction/azeotropic distillation approaches have also been disclosed. These methods all have significant failings. The extraction processes typically generate little waste, even though the highly reactive nature of chloral can produce side reactions with most of the solvents suggested in the prior art. These types of processes are, however, inherently substantial energy consumers, which adversely affects their economics. Flammability and toxicity of the solvents, and contamination of the chloral product by the solvents, are also problems. The contamination problem may prohibit pharmaceutical use of chloral purified through these methods, depending on the particular solvent used.

The prior art sulfuric acid or oleum approaches to chloral purification generate substantial quantities of waste sulfuric acid. The object of this invention is to reduce the strength of the waste sulfuric acid generated by drying chloral to a 40- to 50-percent sulfuric acid concentration while still producing product within the present commercial specification of 0.2 weight percent water. This reduction in the strength of the waste acid produces a significant reduction in the amounts of concentrated acid required for the process versus that required by the most efficient of the prior art processes. This is accomplished through intentional inversion of liquid phases, a unique feature of this invention.

A further object of the invention, therefore, is the reduction in the amount of waste sulfuric acid resulting from the purification process.

A third object of this invention is to accomplish removal of acidity, mainly HCl acidity, in the sulfuric acid-contacting portion of the process, and eliminate any need to remove this acidity by distillation, or other means, later in the purification process.

The objects of this invention are accomplished by the process disclosed herein.

SUMMARY OF THE INVENTION

The invention comprises a process of purifying wet crude chloral derived from acetaldehyde chlorination. In the practice of the invention, HCl acidity is removed in the first sulfuric acid-contacting operation through the practice of "refluxing" the boiling mixture of sulfuric acid and chloral solutions. The process comprises:
 (a) contacting the crude chloral with a sulfuric acid solution having a concentration necessary to produce a two-phase solution wherein the sulfuric acid forms the top phase after agitation;
 (b) separating the phases to recover the chloral phase; and
 (c) contacting the chloral recovered in (b) with more concentrated sulfuric acid to obtain the dried product.

The invention further comprises countercurrently cycling the sulfuric acid solution recovered from (c) to (a) to be used in the initial contacting of more crude chloral.

DETAILED DESCRIPTION OF THE INVENTION

Figure 2:
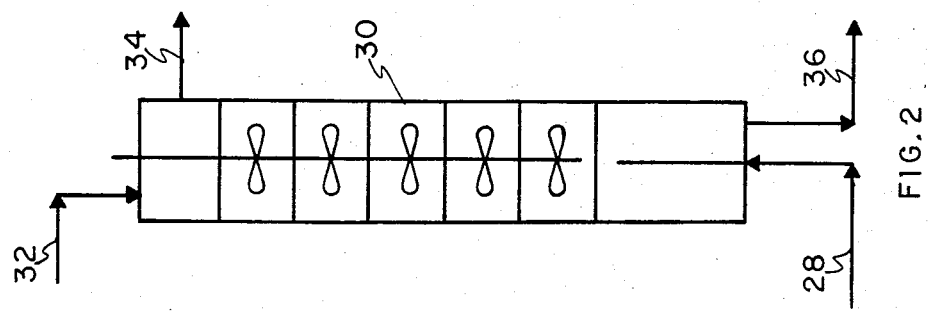
FIG. 2 is a schematic illustration of another embodiment of the invention.

The invention comprises an improved method of countercurrent contacting of sulfuric acid and wet crude chloral produced by the chlorination of acetaldehyde to purify the chloral.

The invention further comprises a process wherein a significantly reduced amount of sulfuric acid is required to produce a purified chloral product with low water and HCl contents. Water and HCl analyses of less than about 0.2 percent each are typically obtained.

Crude chloral within the scope of this invention is herein defined as the unpurified product of acetaldehyde chlorination conducted in an aqueous medium. This material consists primarily of chloral, water, dissolved HCl, and such commonly found contaminants as monochloroacetaldehyde, dichloroacetaldehyde, butyl chloral, the chloroacetic acids, carbon tetrachloride, and chloroform. Other contaminants may be present, depending on the method in which the chlorination is practiced, but the presence of such contaminants normally will not limit the utility of this invention. Likewise, acetaldehyde in different forms can be used. The prior art disclosed in U.S. Pat. Nos. 2,702,303 and 2,768,173 describes the use of acetaldehyde and its reversible polymers (e.g. paraldehyde, $(CH_3CHO)_3$, the former disclosing a completely aqueous process which is the usual commercial practice, and the latter disclosing a process of anhydrous chlorination of paraldehyde to the hexachloroparaldehyde state, followed by aqueous chlorination to crude chloral. The practice of either of these inventions, or such variations which will occur to those skilled in the art to produce crude chloral as described above, will produce crude chloral amenable to purification by the practice of this invention.

An additional feature, which can optionally be used in the practice of the invention, is the use of additional stages within each contacting operation. This produces drier chloral for a given consumption of fresh sulfuric acid than is the case if the one-stage-per-contacting-operation method of the basic process is used.

The chloral solution from the final contacting operation can be used immediately in processes which can tolerate its sulfuric acid content and whatever organic contaminants it may contain, or may be further purified by distillation. Improvements in chlorination technique have been such that organic contaminants are generally minimal; simple distillation to remove the sulfuric acid content should be all that is normally required.

In the process disclosed herein wet, crude chloral is contacted in a countercurrent process with sulfuric acid. In this countercurrent process, crude chloral is contacted with sulfuric acid in such a manner that two contacting operations are utilized which may each comprise a plurality of contacting stages. Use of the two distinct contacting operations is necessitated by a liquid-phase inversion characteristic to the chloral-water-sulfuric acid system.

The term "countercurrent contacting" is defined herein as the opposite or substantially opposite flows of the materials being contacted.

The terms "stage" and "multistage" are defined herein as taking their usual chemical engineering meanings. In general a stage for the liquid-liquid contacting operations described herein will be comprised of a contacting step in which the solutions are mixed together, followed by a separation step in which the resulting solutions are separated. The separation of the resulting solutions in a continuous multistage operation as exemplified by FIG. 2 would, however, be accomplished by the flow of the acid to the bottom of the column as the chloral vapor or liquid rises through the column. Two possible means of accomplishing the separation step are separation by liquid-phase separation, and separation by distillation of the chloral from the sulfuric acid solution. This invention consists mainly of the discovery that liquid-phase separations at lower sulfuric acid strengths than previously thought feasible are possible and that improved results can be obtained by making the first contacting step separations in this manner. However, the distillation separation embodiment is intended to be an embodiment of the present invention.

The utility of the distillation approach is aided by the generally low volatility of sulfuric acid solutions in general, but the water vapor pressure exerted by such solutions increases drastically at strengths below 65 percent. Much of the dehydrating ability of the process is consequently lost if one attempts to discharge waste sulfuric acid solution below 65 percent in strength while making the separations by distillation. The vaporizing chloral solution sweeps the water vapor exerted by the sulfuric acid solution with it as it leaves the mixture, and results in a wetter chloral solution than if the separation had been made by decanting.

Liquid-phase separation is dependent on immiscibility of the solutions being separated, and upon their specific gravity differences. The utility of this approach is complicated somewhat by a phase inversion which takes place in the 52 to 57 (wt.) percent sulfuric acid strength region (organic-free basis). The inventions of the prior art which used liquid-phase separation were all limited to operations at strengths above the phase inversion. The actual concentration at which the inversion takes place will be affected by the type and amounts of impurities (other than water) which may be present in either phase, particularly by low-specific-gravity organic contaminants which may be found in the chloral. The sulfuric acid solution becomes the lighter phase at concentrations below the inversion. Chloral becomes a significant component in the sulfuric acid at these lower strengths; a typical analysis for a 50-percent sulfuric acid solution (on an organic-free basis) is 45 (wt.) percent each water and sulfuric acid as $H_2SO_4$, and 10-percent chloral. Liquid-phase separation is lost altogether as sulfuric acid concentrations decrease below 40 percent (again on an organic-free basis), with the exact concentrations where separation is lost variable with the specific sulfuric acid-chloral-water ratios of different mixtures. Dehydrating ability of the sulfuric acid is lost before loss of liquid-phase separation; therefore, the locus of points where separation is lost is not of much importance in practicing this invention. Temperature has a marked effect on the water removal efficiency of liquid-phase separation. Chloral hydrate decomposition is incomplete at temperatures below 72° C.; the material must therefore be kept above about 72° C. until after decanted or the hydrate will decrease the drying attained at any given sulfuric acid strength. The lower energy requirements of, and lower water content of chloral solutions obtained by, the liquid-phase separation method will generally make it preferred over the distillation alternative in performing the separation (b).

In practice of this invention, the strength of the sulfuric acid solution generated in the first contacting operation of the invention will be below the liquid-phase inversion concentration range. The usual strength of this sulfuric acid solution will be from about 32 to about 52 percent and preferably from about 40 to about 50 percent (organic-free basis). The separation is then made by liquid-phase separation.

The wet crude chloral is generally mixed batchwise with the sulfuric acid solution which preferably is comprised of the effluent from the second contacting operation of a prior production. The mixture is agitated, heated, and refluxed to remove hydrogen chloride. It may be necessary to add some fresh sulfuric acid in addition to the second contacting operation effluent material depending on the water content of the crude chloral feed and the strength of the second-stage effluent acid solution.

Refluxing is continued until HCl gas evolution is minimal or sampling of the mixture indicates sufficient HCl removal.

Sulfuric acid solutions, even at the low concentrations used in the practice of this invention, have the ability to force hydrogen chloride gas from the crude chloral. It is postulated that the water content of this crude chloral bonds the HCl to it, and such bonding is lost upon contact with sulfuric acid solutions because of the desiccating action of the sulfuric acid. A typical use of this phenomena, offered as an illustration, not limitation, is a combination of crude chloral containing dissolved HCl with sulfuric acid to produce a mixture with the sulfuric acid strength below the inversion point. Agitation and heating evolve HCl gas from which chloral can be condensed and returned to the mixture. Following this procedure for a reasonable period reduces the HCl content of the chloral phase of the mixture to 0.15 (wt.) percent or below. The HCl concentration can be further reduced through use of prolonged treatment times. Use of sulfuric acid of reduced strengths also has the additional benefit, noted in the prior art, of removing water-soluble materials, notably the chloroacetic acids, which may be present in crude chloral from acetaldehyde chlorination.

The chloral is recovered from this first contacting operation, as previously indicated, by liquid-phase separation. Simple separation of the liquid phase is generally used after agitation has ceased. The sulfuric acid solution should comprise the top phase but, as previously indicated, a phase inversion occurs in the 52 to 57 weight percent sulfuric acid strength range. Because of the negligible specific gravity difference of the solutions within the inversion concentration range, liquid-phase separations are very slow, if not wholly impractical. Ensuring that one is below the inversion range is therefore very important.

In the second contacting operation or (c) of the disclosed process, the chloral separated from the first contacting operation is contacted with concentrated sulfuric acid to remove essentially all of the remaining water. This can be done with the chloral either as a liquid or a vapor. If done with the chloral as liquid, agitation and heating are required to facilitate this operation; any remaining HCl gas in the chloral solution can be vented from the contacting operation. Heating is generally accomplished to above 72° C. and preferably to reflux. After agitation has ceased the dried purified chloral is recovered by liquid-phase separation wherein the strength of the sulfuric acid solution is above the liquid-phase inversion range and therefore the sulfuric acid forms the lower phase.

In Examples 1 and 2 following, separations were performed exclusively by liquid-phase separations, decanting for instance. As has been discussed, distillation is a possible alternate means of accomplishing these separations, but use of distillation is usually not desirable at the lower sulfuric acid concentrations because the resulting chloral solution is much wetter than if the separation is performed by liquid-phase decanting. However, use of distillation, or various other vapor phase approaches, can be used to advantage at higher sulfuric acid solution strengths such as those typical of the second contacting operation (c) of this invention.

A simple embodiment of the process of Example 1 would use separation by distillation to advantage in most instances. Distillation is usually necessary after the second contacting operation (c) to prevent polymerization; use of distillation directly from the mixture without any intervening decanting step simplifies the process, and is probably indicated unless the end use of the chloral product is immediate and can tolerate a residual sulfuric acid content. Energy conservation favors decanting in the latter case.

An embodiment along similar lines to the multistage, countercurrent approach to operation (c) as practiced in Example 2 is also possible. The chloral solution resulting from the liquid-liquid separation (b) can be vaporized and contacted with sulfuric acid while in the vapor phase, this being the modified approach to operation (c). Countercurrent, multi-stage operations analogous to the liquid-liquid extraction column of Example 2 can be obtained with the chloral in the vapor phase by using a countercurrent scrubbing column, or a countercurrent arrangement of columns in which circulating sulfuric acid of progressively higher strengths contacts the chloral. The choice between these alternates will be dictated by the objectives of the user and the mechanical limitations of the equipment, but the main objective is the same in either case, countercurrent scrubbing and drying of the chloral vapor by the sulfuric acid. This modification has the advantages of simplifying the overall process and allowing the improved process control generally typical of a scrubbing column versus a liquid-liquid extraction column on the plant scale of operation. The dried chloral vapor can be condensed to sulfuric acid-free liquid product directly as in the case in the preceding paragraph.

Example 3 shows the large increase in sulfuric acid usage and waste with higher waste acid strengths; maintaining low sulfuric acid usage requires making the first contacting and separation operations with the chloral in the liquid phase. Choice between liquid-liquid and vapor-liquid contacting in the balance of the process will depend on the circumstances of the user, since what would be optimum for one may not be for another.

Variations of the purely countercurrent flow arrangement will occur to those skilled in the art, and may be necessary, as in Example 1, below, to make adjustments necessitated by variations in the feed stocks to the process, or accomplish other objectives. Such variations are to be regarded as within the spirit of this invention.

If consistent production of chloral product containing a water content below 0.5 percent while using the minimum possible amount of sulfuric acid is desired, multi-stage contacting may be performed within each of the two disclosed contacting operations. This can be accomplished through using the same or similar equipment to that as shown in Example 2 or other means known in the art. Each contacting operation can be, therefore, comprised of a plurality of contacting stages.

The chloral content of the waste sulfuric acid generated in the first contacting operation of the process of the invention can be recovered by simple distillation. If done batchwise, from wastes in the 40 to 50% sulfuric acid strength range, the initial overhead product is almost pure chloral hydrate. A sharp rise in the still temperature will correspond to exhaustion of most of the chloral from the still and the overhead product becoming mostly water. A sharp separation is possible using only simple batch distillation; chloral concentrations below one percent (wt.) were obtained with chloral concentrations in the cumulative overhead above 50 percent (wt.). Although multi-stage and continuous distillation can be used to do this operation, such would not seem to be necessary or desirable in view of the good separation obtained by simple distillation.

As previously indicated, various equipment and flow schemes can be used to contact the sulfuric acid and chloral solutions. Examples of two (continuous liquid-liquid extraction column and a batchwise mixer-settler system) are offered by way of illustration, not limitation.

EXAMPLE 1

Figure 1:
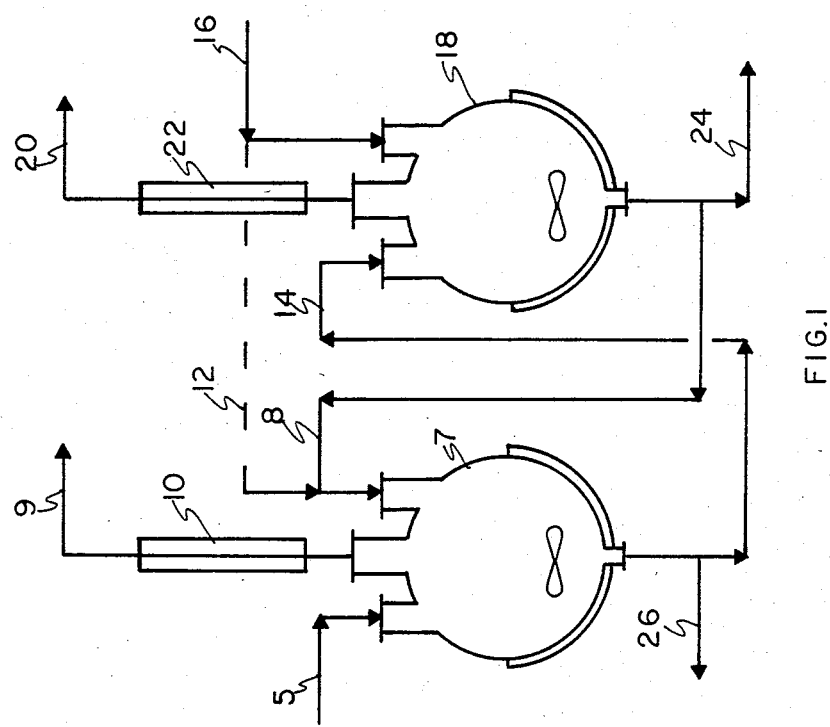
FIG. 1 is a schematic illustration of an embodiment of the invention.

Wet, acidic, crude chloral from acetaldehyde chlorination was purified in a batchwise process as shown in FIG. 1. In (a) the crude chloral solution via line 5 was contacted in mixer vessel 7 with a sulfuric acid solution (the effluent sulfuric acid from a previous batch introduced via line 8) with agitation and heating to remove hydrogen chloride acidity via line 9 utilizing reflux condenser 10.

Specifically, in (a), 1045 grams of crude chloral and 160 grams of a sulfuric acid solution recovered from operation (c) of a previous batch containing 73.5 percent $H_2SO_4$ were combined and heated to boiling with agitation in mixer 7. No appreciable generation of HCl gas was observed, and when allowed to settle, a single liquid phase was observed. This material was analyzed and found to contain:

| Water | 22.97% (wt.) |
|---|---|
| Sulfuric Acid ($H_2SO_4$) | 9.48% |
| Hydrogen Chloride (HCl) | 3.24% |
| Chloral (by difference) | 64.31% |

To appreciably remove the hydrogen chloride acidity 63 grams of additional sulfuric acid, having a concentration of 96.8 wt. percent, was added via line 12 to 1000 grams of the above mixture which was again boiled and agitated. Evolution of HCl gas was observed. Condensible material carried by the HCl gas was condensed by the reflux ("knock-back") condenser 10, and returned to the mixture. Operation (a) was terminated when generation of HCl decreased to a minimal rate.

In (b) a simple liquid-phase separation of the mixture obtained from (a) was accomplished after agitation ceased. The sulfuric acid solution formed the top phase and had a strength of 36.6% as $H_2SO_4$.

In (c) a charge of 600 grams of the chloral solution from (b) was introduced via line 14 into mixer vessel 18 and combined with 160 grams of 96.8 percent sulfuric acid introduced via line 16. The mixture was heated to 90° C. and agitated, then held for 20 minutes. A small amount of HCl gas was vented via line 20 from reflux condenser 22. Agitation was stopped and the phases separated. The sulfuric acid solution formed the bottom phase in this separation. The chloral solution was obtained via line 24. Its sulfuric acid content was 0.25 wt. percent. Further purification by simple distillation would be required to prevent polymerization by the sulfuric acid in the event that the chloral so obtained is stored for any extended period of time (e.g., generally longer than about 12 hours).

The following data were obtained upon completion of (c) and separation of the phases by decanting.

| | Separated Phases | |
|---|---|---|
| | Chloral Phase (540 g) | Acid Phase (217 g) |
| % $H_2O$ | 0.31 | 23.38 |
| % $H_2SO_4$ | 0.25 | 73.49 |
| % HCl | 0.17 | 0.29 |
| % Chloral* | 99.27 | 2.84 |

*Chloral percentages calculated by difference in all cases, and include organic contaminants of the crude chloral.

The waste sulfuric acid from the disclosed process (a) was removed via line 26.

EXAMPLE 2

The chloral phase obtained from an initial contacting and separation operations similar to (a) and (b) of Example 1 was fed via line 28 to a countercurrent liquid-liquid extraction column 30 shown in FIG. 2 and contacted with 90-percent sulfuric acid from a countercurrent feed introduced via line 32. A total of 1000 ml of (b) effluent chloral solution was fed to column 30 during a 72-minute period. The sulfuric acid flow was regulated to maintain a 70-percent exiting sulfuric acid concentration. The column temperature was maintained at 80° to 85° C. to ensure chloral hydrate decomposition.

The following data were obtained during the operating period:

| Elapsed Time | Water in Chloral | Sulfuric Strength |
|---|---|---|
| 4 minutes | 0.12% | 68.47% |
| 24 minutes | 0.08% | 68.43% |
| 48 minutes | 0.07% | 69.96% |
| 64 minutes | 0.08% | 71.17% |

Using the extraction column as disclosed in FIG. 2 produced a drier chloral product and discharged a lower strength sulfuric acid than those obtained in (c) of Example 1.

The purified, dry chloral was recovered via line 34 while the sulfuric acid phase was recovered via line 36 for reuse in (a) of a subsequent initial contacting operation.

EXAMPLE 3

The following is a comparison of sulfuric acid usages as in the above Examples with those required by methods of the prior art, which shows the marked decrease obtainable in such usage through practice of this invention. In all cases below, it is assumed one starts with crude chloral containing 15 percent water and negligible HCl, and 98 percent sulfuric acid. Approximate sulfuric acid usage at several discharge strengths, compared to practice of this invention discharging acid solution at 45 percent:

| Acid Strength at Discharge | Kg of Acid at 98% strength per Kg of Chloral Product |
|---|---|
| 85%* | 1.14 |
| 70%* | 0.434 |
| 60%* | 0.275 |
| 45% | 0.148 |

*These strengths represent the prior art.

The marked decrease in fresh acid required is easily seen. These usage figures can, of course, be further decreased by using oleum as a feedstock. Generally, oleum or sulfuric acid of greater than about 80% is suitable for use in practicing the second contacing operation. A strength of 90% is desirable. It is not desirable to utilize oleum or sulfuric acid much stronger than 90 percent in a countercurrent liquid-liquid extraction column as illustrated in Example 2 because of possible polymerization and decomposition problems. The reduced requirements of the invention for fresh sulfuric acid can be maintained, however, by recycling a portion of one of the weaker sulfuric acid solutions from the process to dilute the fresh concentrated sulfuric acid or oleum to the desired feed strength for the countercurrent liquid-liquid extraction column using methods well known to those skilled in the art.

I claim:

1. A process for purifying wet crude chloral using sulfuric acid in a plurality of contacting operations wherein the contacting and separating are conducted at a temperature above about 50° C. comprising:
   (a) contacting the crude wet chloral with a sulfuric acid solution having a concentration necessary to produce two liquid phases wherein the sulfuric acid solution forms the top phase after agitation;
   (b) separating the phases obtained in (a) by physical means;
   (c) contacting the chloral recovered in (b) with a more concentrated sulfuric acid solution to obtain the dried product; and
   (d) countercurrently cycling sulfuric acid solution recovered from (c) to (a) to purify subsequent crude chloral.

2. The process of claim 1 wherein the strength of the sulfuric acid solution after contacting the crude chloral in (a) is from about 32 to 52 percent by weight.

3. The process of claim 2 wherein the strength of the sulfuric acid solution after contacting the crude chloral in (a) is from about 40 to 50 percent by weight.

4. The process of claim 1 wherein the separation of the distinct liquid phases from the first contacting operation is accomplished by decanting.

5. The process of claim 1 wherein hydrogen chloride, and other acidic impurities, are substantially removed from the chloral solution in the first contacting operation.

6. The process of claim 1 wherein the concentration of the sulfuric acid solution supplied to the process in (c) is above about 80 percent sulfuric acid.

7. The process of claim 1 wherein temperature is maintained at from about 50° C. to 97° C.

8. The process of claim 7 wherein the temperature is maintained at from about 72° C. to 85° C.

9. The process of claim 1 wherein a countercurrent liquid-liquid extraction column is used in (c).

10. The process of claim 1 wherein the sulfuric acid solution resulting from the first contacting operation is further treated to recover its chloral content.

11. The process of claim 10 wherein the further treatment, used is distillation.

12. The process of claim 9 wherein the sulfuric acid solution to the extraction column is 80 to 92 percent by weight.

13. The process of claim 9 wherein the sulfuric acid solution strength is 90 percent by weight.

14. A process of claim 1 wherein liquid-phase separation of chloral and sulfuric acid solutions in (a) is accomplished at sulfuric acid strengths below the phase-inversion strength.

15. The process of claim 1 wherein oleum is used to supply sulfuric acid in (c).

16. The process of claim 1 wherein the contacting operations are accomplished using agitation.

17. The process of claim 1 wherein chloral is vaporized after (b) prior to the second contacting operation (c).

18. A process for purifying crude, wet chloral derived from acetaldehyde chlorination using a plurality of contacting operations wherein the contacting and separations are conducted at a temperature above 50° C. comprising:
   (a) contacting the crude, wet chloral with a sulfuric acid solution having a concentration necessary to produce two liquid phases wherein the sulfuric acid solution forms the top phase after agitation;
   (b) separating the phases obtained in (a) by physical means;
   (c) contacting the chloral recovered in (b) with a more concentrated sulfuric acid solution to obtain a dried chloral product.

19. The process of claim 16 wherein the strength of the sulfuric acid solution produced after contacting operation (a) is from about 40 to about 50 parts by weight of sulfuric acid.

20. The process of claim 16 wherein the temperature is maintained at from about 50° C. to about 97° C.

21. The process of claim 16 wherein the temperature is maintained at from about 72° C. to about 85° C.

22. The process of claim 16 wherein separation in (b) is accomplished by decanting.

23. The process of claim 18 wherein the concentration of the sulfuric acid solution supplied to the process in (c) is above about 80% sulfuric acid.

24. The process of claim 18 wherein oleum is used to supply the sulfuric acid in (c).

25. The process of claim 18 wherein the contacting operations are accomplished using agitation.

26. The process of claim 18 wherein chloral is vaporized after (b) prior to the second contacting operation (c).

27. The process of claim 18 wherein a countercurrent liquid-liquid extraction column is used in (c).

28. The process of claim 17 wherein countercurrent contacting of vaporized chloral with liquid sulfuric acid solution is used in (c).

29. The process of claim 26 wherein countercurrent contacting of vaporized chloral with liquid sulfuric acid is used in (c).

30. The process of claim 5 wherein the acidic impurities and hydrogen chloride are removed by refluxing.

* * * * *

UNITED STATES PATENT AND TRADEMARK OFFICE
CERTIFICATE OF CORRECTION

PATENT NO. : 4,513,152
DATED : April 23, 1985
INVENTOR(S) : Richard D. Schillawski It is certified that error appears in the above—identified patent and that said Letters Patent is hereby corrected as shown below: On the title page:
Assignment, change the assignment from "Stauffer Chemical Company, Westport, Conn." to -- Montrose Chemical Corporation of California, Union, N.J. --.
Col. 4, line 53, after "water vapor" insert -- pressure --.
Col. 5, lines 20-21, delete "decanted" and insert -- decantation --.
Col. 9, line 44, delete "contacing" and insert -- contacting --.
Claims 19, 20, 21 and 22, should be dependent from Claim 18 and not Claim 16.

Signed and Sealed this

Eighth Day of October 1985

[SEAL]

Attest:

Attesting Officer

DONALD J. QUIGG

Commissioner of Patents and Trademarks—Designate